United States Patent
Litvin et al.

(10) Patent No.: US 9,824,467 B2
(45) Date of Patent: Nov. 21, 2017

(54) ITERATIVE IMAGE RECONSTRUCTION

(75) Inventors: Andrew Litvin, Stoneham, MA (US); Ram Naidu, Newton, MA (US)

(73) Assignee: ANALOGIC CORPORATION, Peabody, MA (US)

( * ) Notice: Subject to any disclaimer, the term of this patent is extended or adjusted under 35 U.S.C. 154(b) by 81 days.

(21) Appl. No.: 14/130,044

(22) PCT Filed: Jun. 30, 2011

(86) PCT No.: PCT/US2011/042638
§ 371 (c)(1),
(2), (4) Date: Dec. 30, 2013

(87) PCT Pub. No.: WO2013/002805
PCT Pub. Date: Jan. 3, 2013

(65) Prior Publication Data
US 2014/0140601 A1 May 22, 2014

(51) Int. Cl.
*G06T 11/00* (2006.01)
*A61B 6/03* (2006.01)

(52) U.S. Cl.
CPC .......... *G06T 11/005* (2013.01); *G06T 11/006* (2013.01); *A61B 6/032* (2013.01); *G06T 2211/424* (2013.01)

(58) Field of Classification Search
CPC .................. G06T 11/005; G06T 11/006; G06T 2211/424; A61B 6/032
(Continued)

(56) References Cited

U.S. PATENT DOCUMENTS 5,473,657 A 12/1995 McKenna
5,473,876 A 12/1995 Mann et al.
(Continued)

FOREIGN PATENT DOCUMENTS

| JP | 2001286463 | 10/2001 |
| JP | 2006046643 A | 2/2006 |

(Continued)

OTHER PUBLICATIONS

Sunnegardh, Johan. "Iterative Filtered Backprojection Methods for Helical Cone-Beam CT." diss., Linkoping University, 2009. Accessed May 25, 2015. http://liu.diva-portal.org/smash/get/diva2:232734/FULLTEXT01.pdf.*

(Continued)

*Primary Examiner* — Utpal Shah
(74) *Attorney, Agent, or Firm* — Cooper Legal Group, LLC

(57) ABSTRACT

One or more techniques and/or apparatuses described herein provide for reconstructing image data of an object under examination from measured projection data indicative of the object. The measured projection data is converted into image data using an iterative image reconstruction approach. The iterative image reconstruction approach may comprise, among other things, regularizing the image data to adjust a specified quality metric of the image data, identifying regions of the image data that represent aspects of the object that might generate inconsistencies in the measured projection data and correcting the measured projection data based upon such an identification, and/or weighting projections comprised in the measured projection data differently to reduce the influence of projections that respectively have a higher degree of inconsistency in the conversion from projection data to image data.

20 Claims, 6 Drawing Sheets

(58) Field of Classification Search
USPC .......................................................... 382/131
See application file for complete search history.

(56) References Cited

U.S. PATENT DOCUMENTS

| | | | |
|---|---|---|---|
| 5,851,327 A | 12/1998 | Landin | |
| 6,823,037 B2 | 11/2004 | Riemer et al. | |
| 2002/0146088 A1 | 10/2002 | Riemer et al. | |
| 2003/0076988 A1* | 4/2003 | Liang ........................ | G06T 5/10 382/131 |
| 2005/0175143 A1* | 8/2005 | Miyazaki ............... | A61B 6/032 378/19 |
| 2006/0056685 A1* | 3/2006 | Kiraly et al. .................. | 382/165 |
| 2006/0140482 A1* | 6/2006 | Koehler ......................... | 382/193 |
| 2008/0273651 A1* | 11/2008 | Boas ................................ | 378/4 |
| 2009/0052762 A1* | 2/2009 | Dugan et al. .................. | 382/132 |

FOREIGN PATENT DOCUMENTS

| | | |
|---|---|---|
| JP | 2007048726 A | 2/2007 |
| JP | 2009046643 A | 3/2009 |
| JP | 2009510400 A | 3/2009 |
| JP | 2011024866 A | 2/2011 |

OTHER PUBLICATIONS

International Search Report cited in related application No. PCT/US2011/042638 dated Jun. 26, 2012, pp. 13.
Sunnegardh, Johan, "Iterative Filtered Backproject i on Methods for Helical Cone-Beam CT", Sep. 1, 2009, Linkoping University Electronic Press, Linkoping, XP055018986, ISBN: 978-9-17-393586-9 Chapter 2, sec. 2.2, "Weighted filtered backprojection" ; p. 13 Chapter 5, Regularized iterative weighted filtered backprojection; p. 45-p. 69.
Fessler, J. A., "Iterative Methods for Image Reconstruction", ISBI 2006 Tutorial, www.eecs.unich.edu/ fessler/papers/files/talk/06/isbi,p1,note.pdf, 2006. pp. 1-79.
Feldkamp, et al., "Practical cone-beam algorithm", J. Opt. Soc. Am., vol. 1 No. 6, Feb. 28, 1984, pp. 612-619.
Preliminary Amendment cited in U.S. Appl. No. 14/130,001 dated Mar. 15, 2012, 9 pgs.
Int. Search Report cited in PCT Application No. PCT/US2011/042567 dated Mar. 15, 2012, 11 pgs.
Korean Office Action cited in Japanese Application No. 2014-518517 dated Mar. 3, 2015, 4 pgs.
Preliminary Amendment cited in U.S. Appl. No. 14/130,001 dated Mar. 15, 2012, 7 pgs.
Korean Office Action cited in Japanese Application No. 2014-518519 dated Mar. 3, 2015, 4 pgs.
EP Communication cited in EP Application No. 11730538.3 dated Jun. 25, 2015, 4 pgs.
Reply EP Communication cited in EP Application No. 11730538.3 dated Oct. 19, 2015, 23 pgs.
EP Communication cited in EP Application No. 11730538.3 dated Nov. 9, 2015, 4 pgs.
Reply EP Communication cited in EP Application No. 11730538.3 dated Feb. 23, 2016, 3 pgs.
EP Office Action cited in EP Application No. 11730538.3 dated Mar. 31, 2016, 3 pgs.

* cited by examiner

ITERATIVE IMAGE RECONSTRUCTION

BACKGROUND

The present application relates to image reconstruction, such as may be performed by computed tomography (CT) scanners, for example. It finds particular use in medical, security, and/or industrial applications where image data is reconstructed from projection data using an iterative reconstruction technique.

Radiographic imaging systems, such as CT systems, provide information and/or images of an object under examination or interior aspects of the object. For example, in radiographic imaging systems, the object is exposed to radiation, and one or more images are formed based upon the radiation absorbed by the object or an amount of radiation that is able to pass through the object. Typically, highly dense objects absorb (e.g., attenuate) more radiation than less dense objects, and thus an object having a higher density, such as a bone or metal plate, for example, will appear differently than less dense objects, such as skin or clothing, for example.

Today, there are numerous types of radiographic imaging systems. One of the more versatile types of radiographic imaging systems is a CT scanner. CT scanners are used in a variety of fields and are used to identify a plurality of characteristics and/or features about an object under examination. For example, security CT scanners can determine the chemical composition of an object under examination and/or can identify markers (e.g., density, shape, etc.) that are commonly associated with threat items. In medical applications, CT scanners can be used to generate images of a variety of aspects of a patient. For example, some CT scanners are configured to distinguish between gray matter and white matter in the brain, while other CT scanners are configured to image arteries and/or the heart.

One of the features that have made CT scanners so versatile is their ability to record X-ray projections (e.g., views) of an object from a plurality of positions (e.g., generally covering at least a 180 degree angular range) and to employ an image reconstruction algorithm(s) to generate two-dimensional and/or three-dimensional images indicative of the object.

To view an object under examination from a plurality of angles, a typical CT scanner comprises a radiation source and a detector array that are mounted on a rotating gantry comprising a central opening (e.g., a bore) large enough to receive the object (e.g., a patient, luggage, etc.). During the examination of the object, the rotating gantry, including the radiation source and/or the detector array, is rotated about the object and radiation is emitted from the radiation source. By rotating the radiation source relative to the object, radiation is projected through the object from a plurality of different positions, and the detector array generates measured projection data indicative of the amount of radiation it detects.

Image reconstruction algorithms are used to reconstruct volumetric images (e.g., density images, z-effective images, etc.) from the projection data generated by the detector array. Today, image reconstruction algorithms can be broadly classified into analytical algorithms and iterative algorithms.

Analytical image reconstruction algorithms, such as Filtered Back-Projection, Feldkamp David Kress algorithm, etc., reconstruct images from measured projection data using deterministic formulas that usually approximate an algebraic inversion of a CT projection transform. The projection transform is a mathematical formula that describes the signal or photon count recorded by the detector array as a function of the volumetric density image.

Analytical image reconstruction algorithms are commonly used in CT applications due to their speed, predictable and controllable properties, and/or ease of implementation. However, analytical algorithms have several limitations. For example, this approach assumes noise-free, ideal "line integral" projection data without inconsistencies due to the physics of x-ray propagation and/or acquisition. Additionally, because image voxels are reconstructed independently from input projection data, constraints are imposed on data acquisition protocols and/or detector array design (e.g., by not allowing for missing data), for example. Data inconsistencies and imperfections (e.g., such as due to beam hardening) may lead to image artifacts. Further, analytic image reconstruction algorithms generally treat all measured photon counts uniformly regardless of the validity of these counts, resulting in suboptimal noise characteristics, for example, and generally provide merely approximations for some conversion operations, resulting in geometric artifacts, for example.

Iterative image reconstruction algorithms reconstruct an image through successive image refinements, so that expected (e.g., synthesized) projections computed from the reconstructed image substantially match measured projections. At respective iterations, the iterative algorithm forward projects the image, computes synthesized projections, compares the synthesized projection to the measured projection data, and refines the image based upon the difference(s) between the synthesized and measured projection data. It will be appreciated that this process may be repeated until a desired outcome has been reached (e.g., the process has been repeated 20 times, the synthesized projection data is within a particular tolerance of the projection data, etc.).

While iterative image reconstruction algorithms generally have a higher computation complexity, there are numerous benefits to iterative image reconstruction algorithms over analytical image reconstruction algorithms in CT applications. For example, because no mathematical inversion is performed in an iterative algorithm, approximations that generate geometric artifacts are generally avoided. Additionally, the iterative process generally improves noise performance (e.g., iterative reconstruction algorithms can deliver optimal noise performance). Moreover, because iterative image reconstruction algorithms generally do not impose strict rules on data sampling and/or detector geometry, iterative image reconstruction algorithms can be applied to nonstandard data acquisition geometries and/or missing data configurations, for example. Iterative image reconstruction algorithms can also reduce the effects of data imperfections (e.g., such as due to beam hardening and/or other physics effects) and/or improve image quality by including prior information related to properties of the image, such as image non-negativity, for example.

SUMMARY

Aspects of the present application address the above matters, and others. According to one aspect, a method for reconstructing one or more x-ray images of an object under examination from measured projection data indicative of the object is provided. The method comprises converting the measured projection data into image data and regularizing the image data to generate regularized image data by modifying one or more specified quality metrics in the image data. The method also comprises forward projecting the regularized image data to generate synthesized projection data. The method further comprises updating the image data to generate updated image data by comparing the synthesized projection data to the measured projection data.

According to another aspect, a method for reconstructing one or more x-ray images of an object under examination from measured projection data indicative of the object is provided. The method comprises isolating regions of the image data, yielded from the measured projection data, which represent aspects of the object that generate inconsistencies in the measured projection data. The method also comprises forward projecting the isolated regions to generate (e.g., estimate) inconsistent projection data and correcting the measured projection data based upon the inconsistent projection data to generate corrected projection data. The method further comprises updating the image data to generate updated image data using the corrected projection data.

According to yet another aspect, a method for reconstructing one or more x-ray images of an object under examination from measured projection data indicative of the object is provided. The method comprises identifying a degree of inconsistency in measured projections, comprised in the measured projection data, for respective channels of the detector array. The method also comprises weighting (e.g., determining a measure of significance, or a weight for) a first portion of a view comprised in the measured projection data differently than a second portion of the view based upon the identified degree of inconsistency in respective measured projections.

According to yet another aspect, a method for reconstructing one or more x-ray images of an object under examination from measured projection data indicative of the object is provided. The method comprises regularizing the image data to generate regularized image data and forward projecting the regularized image data to generate synthesized projection data. The method also comprises isolating regions of the regularized image data that represent aspects of the object that generate inconsistencies in the measured projection data and forward projecting the isolated regions of the regularized image data to generate (e.g., estimate) inconsistent projection data. The method further comprises correcting the measured projection data based upon the inconsistent projection data to generate corrected projection data. The method also comprises assigning weights to various portions of at least one of a view comprised in the measured projection data and a view comprised in the corrected projection data, a first portion of the view comprised in the measured projection data weighted different than a second portion of the view comprised in the measured projection data and a first portion of the view comprised in the corrected projection data weighted different than a second portion of the view comprised in the corrected projection data. The method also comprises updating the image data to generate updated image data based at least in part upon the synthesized projection data and at least one of the measured projection data, the corrected projection data, the weights assigned to various portions of the view comprised in the measured projection data and/or the weights assigned to various portions of the view comprised in the corrected projection data.

According to yet another aspect, a system for reconstructing an x-ray image of an object under examination from measured projection data indicative of the object under examination is provided. The system comprises an image updater configured to convert the measured projection data into image data representative of the object. The system also comprises an inconsistency detector configured to isolate regions of the image data that represent aspects of the object that generate inconsistencies in the measured projection data. The system also comprises a forward projection component configured to forward project the isolated regions of the image data to generate inconsistent projection data and a projection correction component configured to correct the measured projection data based at least in part upon the inconsistent projection data to generate corrected projection data. The image updater is also configured to update the image based at least in part upon the corrected projection data.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
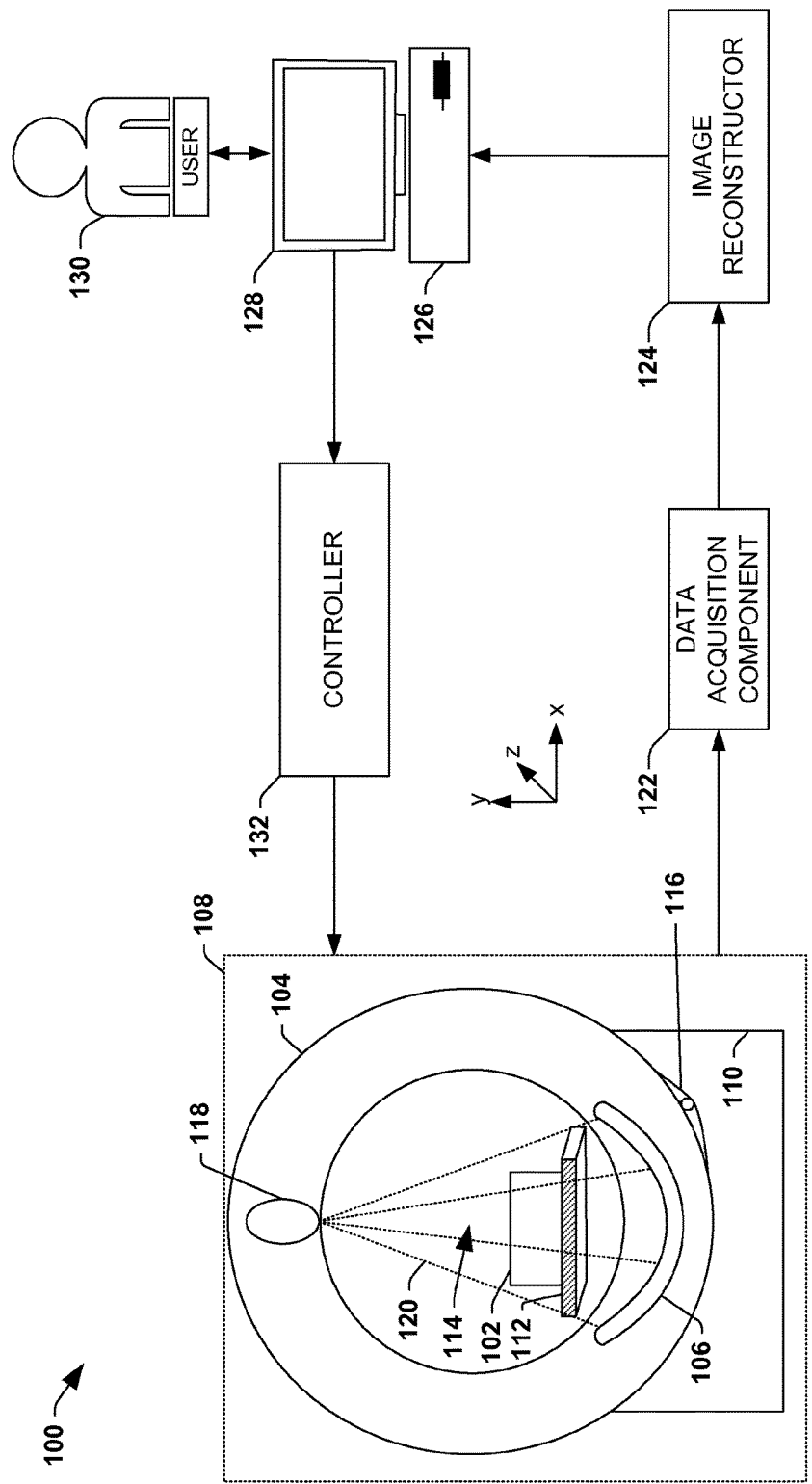
FIG. 1 is a schematic block diagram illustrating an example environment for reconstructing images from measured projection data.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to an iterative image reconstruction technique such as may be performed to reconstruct images of an object examined by a computed tomography (CT) scanner, for example. It also relates to a system for image reconstruction. The techniques and/or systems disclosed herein comprise iteratively updating an image until a specified outcome has been achieved. During respective iterations, the image(s) may be regularized (e.g., filtered) to modify one or more specified quality metrics of the image(s), regions of the image(s) that represent aspects of the object that generate inconsistencies in projection data (e.g., such as high density aspects of the object) may be isolated, and/or inconsistencies in the projection data may be identified and selectively suppressed while creating the image(s), for example. It will be appreciated that while specific reference is made herein to using the techniques and/or systems in conjunction with computed tomography scanners, the instant disclosure, including the extent of the claims, is not intended to be so limited to the extent practical. That is, for example, the technique(s) and/or system(s) described herein may be used in other applications, besides CT applications, where generating an image(s) from projection data using iterative image reconstruction algorithms would be useful.

FIG. 1 is an illustration of an example environment 100 in which iterative image reconstruction techniques and/or systems as described herein may be useful. More particularly, FIG. 1 illustrates an example computed tomography (CT) apparatus that can be configured to acquire volumetric information regarding an object 102 under examination and generate two-dimensional and/or three-dimensional images therefrom. It will be appreciated that the example environment 100 merely illustrates an example schematic and is not intended to be interpreted in a limiting manner, such as necessarily specifying the location, inclusion, and/or relative arrangement of the components described herein. For example, a data acquisition component 122 as illustrated in FIG. 1 may be part of a rotating gantry 104 portion of the examination apparatus 108, or more particularly may be part of a detector array 106, for example.

In the example environment 100, an object examination apparatus 108 is configured to examine one or more objects 102 (e.g., a series of suitcases at an airport, a patient, etc.). The object examination apparatus 108 can comprise a rotating gantry 104 and a (stationary) support structure 110. During an examination of the object(s) 102, the object(s) 102 can be placed on a support article 112, such as a bed or conveyor belt, for example, that is selectively positioned in an examination region 114 (e.g., a hollow bore in the rotating gantry 104), and the rotating gantry 104 can be rotated about the object(s) 102 by a rotator 116, such as a motor, drive shaft, chain, etc.

The rotating gantry 104 may surround a portion of the examination region 114 and may comprise one or more radiation sources 118 (e.g., an ionizing x-ray source) and a detector array 106 comprised of a plurality of channels (e.g., also referred to as detectors or pixels) that is mounted on a substantially diametrically opposite side of the rotating gantry 104 relative to the radiation source(s) 118.

The detector array 106 can comprise a linear or two-dimensional array of channels disposed as a single row or multiple rows in the shape of a circular, cylindrical, or spherical arc, for example, having a center of curvature at a focal spot of the radiation source 118 (e.g., the point within the radiation source 118 from which radiation 120 emanates), for example. During an examination of the object(s) 102, the radiation source(s) 118 emits fan, cone, wedge, and/or other shaped radiation 120 configurations from the focal spot and into the examination region 114. It will be appreciated to those skilled in the art that such radiation 120 may be emitted substantially continuously and/or may be emitted intermittently (e.g., a short pulse of radiation is emitted followed by a resting period during which the radiation source 118 is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to strike the detector array 106) than less dense aspects, such as skin or clothing.

As the rotating gantry 104 rotates, the detector array 106 is configured to directly convert (e.g., using amorphous selenium and/or other direct conversion materials) and/or indirectly convert (e.g., using photodetectors and/or other indirect conversion materials) detected radiation into analog signals that can be transmitted from the detector array 106 to a data acquisition component 122 configured to periodically sample the analog signal generated by respective channels and generate a digital output signal representative of one or more characteristics (e.g., density, z-effective, etc.) of a portion of the object 102 being examined during that measuring interval.

The collection of digital output signals generated by the data acquisition component 122 for a measuring interval and yielded from the analog signals respectively output by the channels of the detector array 106 may be referred to by those skilled in the art as a "projection" or a "view". Moreover, the angular orientation of the rotating gantry 104 (e.g., and the corresponding angular orientations of the radiation source(s) 118 and the detector array 106) during generation of a projection may be referred to as the "projection angle".

As the rotating gantry 104 rotates around the object 102 under examination, the data acquisition component 122 generates a plurality of projections at a corresponding plurality of projection angles. It will be appreciated that the term "measured projection data" and/or the like is used herein to refer to this plurality of projections that are generated by the data acquisition component 122 and is indicative of the amount of radiation that the detector array 106 detected or measured.

The example environment 100 further comprises an image reconstructor 124 configured to receive the measured projection data output by the data acquisition component 122. As will be described in more detail, the image reconstructor 124 is configured to use iterative image reconstruction algorithms and/or techniques to generate image data (e.g., which may also be referred to herein as an image, images, CT images, and/or the like) from the measured projection data. In CT, the image is a representation of one or more characteristics (e.g., density, z-effective, etc.) of a two-dimensional "slice" of the object during the rotation of the rotating gantry 104 through the various projection angles. In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive user input from the terminal 126 and generate instructions for the object examination apparatus 108 indicative of operations to be performed. For example, the user 130 may want to reexamine the object(s) 102, and the controller 132 may issue a command instructing the support article 112 to reverse direction (e.g., bringing the object(s) 102 back into the examination region 114 of the object examination apparatus 108).

Figure 2:
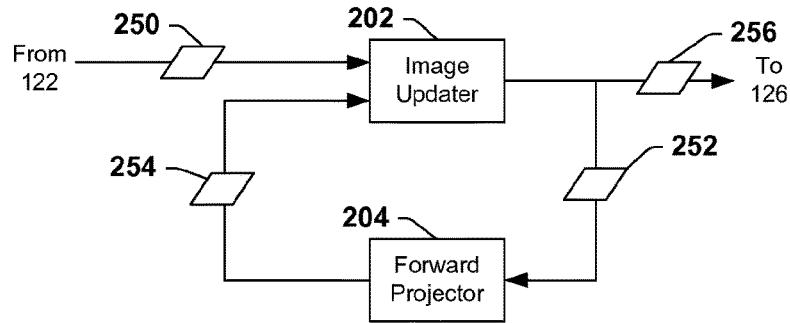
FIG. 2 illustrates a schematic block diagram illustrating an example environment of a conventional iterative image reconstructor.

FIG. 2 illustrates a schematic block diagram of a conventional iterative image reconstructor 200 (e.g., 124 in FIG. 1) that is commonly used to reconstruct images from measured projection data 250. As illustrated, the measured projection data 250 is received from a data acquisition component (e.g., 122 in FIG. 1) at an image updater 202. As will be appreciated by those skilled in the art, the image updater 202 is configured to provide two substantially distinct functions. Initially, when the measured projection data 250 is first received, the image updater 202 is configured to use one or more analytic algorithms known to those skilled in the art to convert the measured projection data 250 into initial image data 252. Subsequently (e.g., once image data 252 has been initially created), the image updater 202 is configured to update the image data 252 by comparing the measured projection data 250 to synthesized projection data 254 (e.g., described hereforth). That is, the image updater 202 is configured to generate image data 252 during an initial pass (e.g., using a first set of one or more algorithms) and is configured to update the image data 252 (e.g., using a second set of one or more algorithms) yielded from the previous pass during subsequent passes. The algorithm(s) used to generate the image data 252 and the algorithm(s) used to update the image data 252 may be the same or different algorithms. It will be appreciated that for simplicity in the figures, the initial image data and updated image data (e.g., that is generated at successive iterations after the initial image data is generated) are both referenced by character reference 252.

Those skilled in the art will understand that the analytic algorithms (e.g., 2D filtered back projection, 3D filtered back projection, etc.) attempt to approximate the initial image data 252 from the measured projection data 250. That is, it is generally not certain during the conversion of the measured projection data 250 to the image data 252 that the conversion is precise (e.g., and that forward projecting the image data 252 to projection data would result in the generation of projection data that exactly matches the measured projection data 250). Thus, the initial image data 252 may comprise visible reconstruction artifacts, for example, that may degrade the quality of the image data 252 and/or render the image data 252 useless for its intended purpose (e.g., of identifying potential threat objects).

The example image reconstructor 200 also comprises a forward projector 204 configured to receive the image data 252 and forward project the image data 252 to generate synthesized projection data 254. It will be appreciated that the synthesized projection data 254 is indicative of the projection data that would have generated the (e.g., potentially artifact possessing) image data 252. That is, if the synthesized projection data 254 were converted to image data, the resulting image data would be the image data 252 (e.g., the synthesized projection data 254 is not an approximation).

Ideally, the synthesized projection data 254 should match the measured projection data 250. Such a match would indicate that assumptions made by the reconstruction algorithm(s) during the conversion of the measured projection data 250 to the image data 252 were accurate and/or that the image is free of reconstruction artifacts. However, because the algorithm(s) merely attempts to approximate the image data 252 from the measured projection data 250, rarely, if ever, do the synthesized projection data 254 and the measured projection data 250 match initially.

Based upon the differences in the synthesized projection data 254 and the measured projection data 250, the image updater 202 adjusts the image data 252 to improve the match between measured projection data and the synthesized projection data. Such an image adjustment(s) may be carried out using gradient decent, Expectation-Maximization and/or other image adjustment approaches known to those skilled in the art. It will be appreciated that the terms "image update" and/or the like may be used herein to describe a process of updating the image data 252 based upon the differences in the synthesized projection data 254 and the measured projection data 250 to generate updated image data.

The acts of forward projecting the image data 252 to generate synthesized projection data 254, and updating the image data 252 based upon a comparison of the measured projection data 250 to the synthesized projection data 254 may be repeated until a specified outcome occurs, at which time the image updater 202 may transmit finalized image data 256 to a terminal (e.g., 126 in FIG. 1). For example, in one embodiment, the acts described above may be repeated a specified number of times (e.g., 20 times). Once that number has been reached, the image updater 202 may transmit the output (e.g., the finalized image data 256) to the terminal. In another embodiment, the repetition may end when the synthesized projection data 254 is within a specified deviation or tolerance of the measured projection data 250 (e.g., the synthesized projection data and the measured projection data are close enough to a match that residual artifacts are de-minimis, additional processing would not be cost effective, etc.).

Thus, FIG. 2 illustrates a conventional iterative image reconstructor 200 that is used to reconstruct image data through successive image refinements, so that expected projections (e.g., the synthesized projection data) computed from the image data 252 substantially matches the measured projection data 250.

Figure 3:
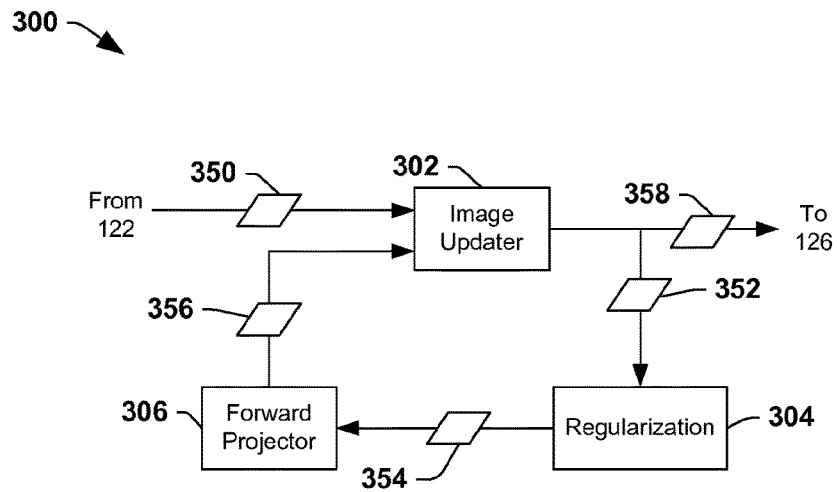
FIG. 3 illustrates a schematic block diagram illustrating an example environment of an image reconstructor.

FIG. 3 illustrates a schematic block diagram of an example image reconstructor 300 (e.g., 124 in FIG. 1) that is configured to reconstruct image data (e.g., images) through successive image refinements as provided herein. Like the image reconstructor 200 illustrated in FIG. 2, the image reconstructor 300 comprises an image updater 302 configured to receive measured projection data 350 from a data acquisition component (e.g., 122 in FIG. 1), for example. As described above, the image updater 302 is configured to provide two substantially distinct functions. Initially, when the measured projection data 350 is first received, the image updater 302 is configured to convert the measured projection data 350 into initial image data 352 using analytic algorithms known to those skilled in the art. Subsequently (e.g., once image data 352 has been initially created), the image updater 302 is configured to update the image data by comparing the measured projection data 350 to the synthesized projection data 356 (e.g., described hereforth) using the same and/or different algorithms relative to those used to initially generate image data 352. For simplicity in the figures, the initial image data and updated image data (e.g., that is generated at successive iterations after the initial image data is generated) are both referenced by character reference 352.

The image reconstructor 300 also comprises a regularization component 304 configured to receive and regularize the image data 352 to generate regularized image data 354. It may be appreciated that the term "regularize" and/or the like is used herein in a broad sense to refer to modifying and/or smoothing, etc. the image data 352 and/or one or more specified quality metrics, such as resolution, modulation transfer function, noise, artifacts, and/or streaks, etc., for example, in the image data 352. For example, regularizing the image data may comprise filtering the image data 352 using a low pass filter to smooth the image data 352. In one embodiment, such low pass filtering may comprise using a linear combination of the image data 352 and a negative Laplacian operator applied to image data 352, for example. However, other filtering techniques or, more generally, regularization techniques known to those skilled in the art for modifying the image data 352 and/or one or more quality metrics of the image data 352 are also contemplated herein.

In one example, suppose the image data 352 is intended to be viewed by a radiologist that is interested in seeing certain structures (e.g., smooth objects) that are visible merely when the image data 352 comprises certain properties. The regularization component 304 may adjust the properties of the image data 352 to generate regularized image data 354 that comprises the certain properties. For example, if the radiologist is interested in viewing smooth aspects of an object (e.g., patient) under examination, the regularization component 304 may reduce noise in the image data 352 while reducing and/or holding constant sharpness of the image data 352. Thus, the regularization component 304 is configured to adjust one or more quality metrics of the image data 352, such as resolution, modulation transfer function, noise, artifacts, and/or streaks, etc. based upon the intended use of a resulting image (e.g., 256 in FIG. 2) that is output by the apparatus, for example.

It will be appreciated that by modifying the image data 352, the regularized image data 354 differs from the image that would have been created by the measured projection data 350 had the measured projection data 350 been perfectly converted into image data (e.g., such that the image data 352 was substantially free of reconstruction artifacts). Thus, the regularized image data 354, and finalized image data 358 that results from the regularization(s) and image update(s) are intended to differ from an idealized image that would be generated from the measured projection data 350.

The image reconstructor 300 further comprises a forward projector 306 (e.g., 204 in FIG. 2) configured to receive the regularized image data 354 and convert, or forward project, the regularized image data 354 to generate synthesized projection data 356 (e.g., 254 in FIG. 2) using forward projection techniques known to those skilled in the art. For example, in one embodiment, the forward projection for a given ray is computed as a sum of the pixels intersected by the ray (e.g., which may be modeled as a stripe). The contribution of respective pixels may be computed as an intersection area (e.g., computed at run-time using a tabulated pixel/stripe intersection area table) between the ray approximated by the stripe and the pixels, for example. However, other techniques for forward projecting image data to generate synthesized projection data 356 are known to those skilled in the art and are contemplated for use herein.

It will be appreciated that as described above, the forward projector 306 generates synthesized projection data 356 that accurately (e.g., exactly) represents the projection data that would have created the regularized image data 354.

The image updater 302 is configured to receive the synthesized projection data 356 and compare it to the measured projection data 350. For example, the comparison of the synthesized projection data 356 and the measured projection data 350 may be based on a cost function, representing a penalty on the data mismatch between the measured projection data 350 and the synthesized projection data 356, and the reconstructed image (e.g., the image update that is applied) may be chosen to reduce and/or minimize the cost function. Possible cost function formulations include, but are not limited to, a Least Squares (LS) formulation and its derivatives and/or Maximum Likelihood (ML) formulation. Other formulations and/or image adjustment approaches, including image update strategies without explicit cost function definitions, are known to those skilled in the art and are also contemplated for use herein.

Based upon the comparison of the measured projection data 350 and the synthesized projection data 356, the image updater 302 may update the image data 352 (e.g., converting the measured projection data 350 to second image data). It will be appreciated that based upon the algorithm(s) used, the pixels of the image data 352 may be updated concurrently and/or in series. For example, in a pixel parallel simultaneous image update scheme, substantially all of the pixels are updated concurrently at respective iterations. However, other pixel update schemes are known to those skilled in the art and are contemplated for use herein.

The acts of regularizing the image data 352, forward projecting the regularized image data 354, and comparing the measured projection data 350 to the synthesized projection data 356 to update the image data by the image updater 302 may be repeated until a specified outcome has been achieved, at which point the image updater 302 may transmit the finalized image data 358 (e.g., 256 in FIG. 2) to a terminal (e.g., 126 in FIG. 1), for example. Stated differently, the image updater 302 may continue to output updated image data 352 and receive synthesized projection data 356 indicative of more recently updated image data 352 to refine the image data 352 (e.g., or the assumptions made in the conversion of the measured projection data 350 to image data 352) until a specified outcome has been achieved. As used herein, a specified outcome references stopping criteria which may comprise, but is not limited to, a specified number of iterations, an acceptable deviation threshold between the synthesized projection data 356 and the measured projection data 350, etc.

It will be appreciated that while the example image reconstructor 300 illustrates a component block diagram that describes the image updater 302 as transmitting the image data 352 to the regularization component 304, in another embodiment, during one or more iterations the image updater 302 may bypass the regularization component 304 and transmit the image data 352 to the forward projection component 306. That is, the image data 352 may be regularized in fewer than all of the iterations. For example, in one embodiment, where the image data 352 is updated twenty times before it is output to the terminal, the image updater 302 may transmit the image data 352 to the regularization component 304 during merely the first and/or last iteration. Thus, during the other eighteen or nineteen iterations, the image updater 302 may transmit the image data 352 to the forward projector 306 (e.g., bypassing the regularization component 304 and not regularizing the image data 352 to generate regularized image data 354 during those eighteen or nineteen iterations). In this way, for eighteen or nineteen of the iterations, the flow diagram may look something like what is illustrated in FIG. 2, while during the first and/or last iteration, the flow diagram may look something like what is illustrated in FIG. 3, for example. It may be appreciated that other than twenty iterations with the first and/or last iterations being "regularized" are contemplated, and that the instant application, including the scope of the appended claims, is not to be limited to these examples (or any other examples set forth herein).

Figure 4:
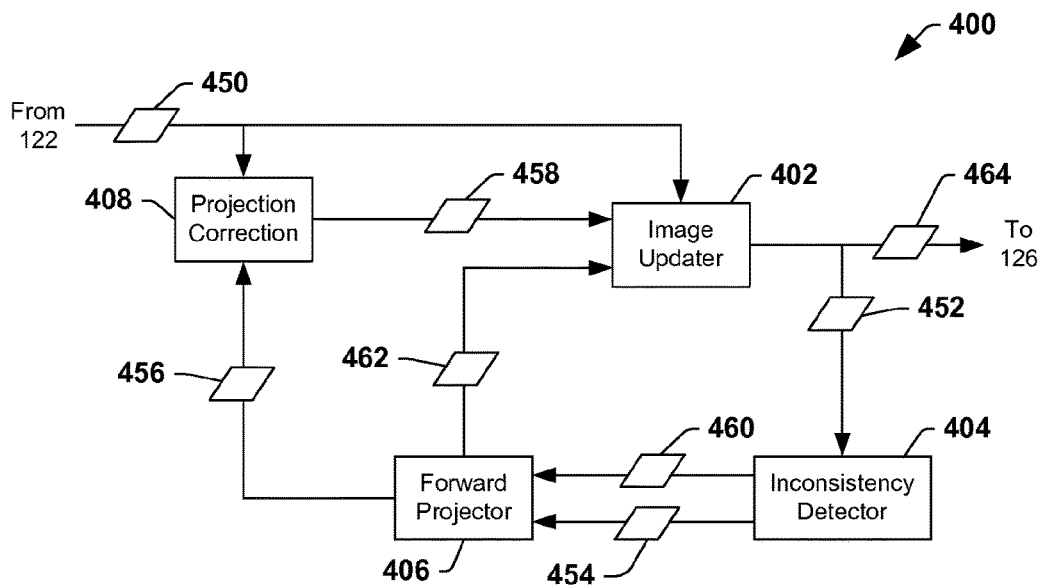
FIG. 4 illustrates a schematic block diagram illustrating an example environment of an image reconstructor.

FIG. 4 illustrates a schematic block diagram of another example image reconstructor 400 (e.g., 124 in FIG. 1) that is configured to reconstruct image data (e.g., images) through successive image refinements. Like the image reconstructor 200 illustrated in FIG. 2, the image reconstructor 400 comprises an image updater 402 (e.g., 302 in FIG. 3) configured to receive measured projection data 450 from a data acquisition component (e.g., 122 in FIG. 1), for example. As described above, the image updater 402 is configured to provide two substantially distinct functions. Initially, when the measured projection data 450 is first received, the image updater 402 is configured to convert the measured projection data 450 into initial image data 452 using analytic algorithms known to those skilled in the art. Subsequently (e.g., once image data 452 has been initially created), the image updater 402 is configured to update the image data 452 by comparing the measured projection data 450 to synthesized projection data 462 (e.g., described hereforth) using the same and/or different algorithms relative to those used to initially generate image data 452. For simplicity in the figures, the initial image data and updated image data (e.g., that is generated at successive iterations after the initial image data is generated) are both referenced by character reference 452.

The image reconstructor 400 also comprises an inconsistency detector 404 configured to identify regions of the image data 452 that represent aspects of an object that generate inconsistencies (e.g., artifacts) in the measured projection data 450 and to isolate the identified regions 454 of the image data 452. It will be appreciated to those skilled in the art that inconsistencies in the measured projection data 450 are generally caused by aspects of the object that have particular characteristics or properties. For example, aspects of the object that comprise materials having a higher density (e.g., such as steel) and/or a higher z-effective (e.g., such as mercury) may create inconsistencies in the measured projection data 450 as a result of photon starvation and/or beam hardening, for example. That is, inconsistencies are created in the measured projection data 450 because of phenomenon that occur when aspects of the object are comprised of certain materials (e.g., high density, high atomic number materials, etc.). For example, high density materials (e.g., such as some metals) absorb a disproportionate amount of lower energy photons causing the high density material to appear in the measured projection data 450 as a lower density material (e.g., that would otherwise allow a substantial number of high energy photons to pass there-through) and resulting in an inconsistency in the measured projection data 450.

The inconsistency detector 404 is configured to identify one or more regions of the image data 452 that represent aspects of the object that generate such inconsistencies and isolate the identified regions (e.g., separating the image data 452 into isolated regions 454 indicative of aspects (e.g., a metal plate) that generate inconsistencies and regions 460 indicative of aspects that generate consistent data). For example, in one embodiment, the inconsistency detector 404 is configured to determine a value for respective voxels or pixels corresponding to a property of the object that causes inconsistencies. For example, the inconsistency detector 404 may determine a CT number (e.g., density value) or z-effective value for respective voxels and/or pixels of the image data 452. The inconsistency detector 404 may then threshold the image data 452 and segment voxels and/or pixels comprised in the image data 452 with values greater than a specified threshold from the image data 452. In this way, the inconsistency detector 404 may be configured to effectively mask aspects of the image data 452 that represent aspects of the object that have a density and/or z-effective, for example, less than or equal to the specified threshold to isolate regions of the image data 452 that represent aspects of the object that have a density and/or z-effective, for example, greater than the specified threshold. That is, the isolated regions 454 of the image data 452 indicative of aspects of the object that generate inconsistencies in the measured projection data 450 are separated from regions 460 of the image data 452 indicative of aspects of the object that do not generate inconsistencies in the measured projection data 450, for example.

The image reconstructor 400 further comprises a forward projector 406 (e.g., 306 in FIG. 3) configured to receive the isolated regions 454 of the image data 452 indicative of aspects of the object that generate inconsistencies in the measured projection data 450 and receive regions 460 of the image data 452 indicative of aspects of the object that do not generate inconsistencies in the measured projection data 450. The forward projector 406 is also configured to convert or forward project the isolated regions 454 and other regions 460 to generate inconsistent projection data 456 indicative of the isolated regions 454 of the image data 452 and synthesized projection data 462 indicative of other, non-isolated, regions 460 of the image data 452 using forward projection techniques known to those skilled in the art. For example, in one embodiment, the forward projection for a given ray is computed as a sum of the pixels intersected by the ray (e.g., which may be modeled by a stripe). The contribution of respective pixels may be computed as an intersection area (e.g., computed at run-time using a tabulated pixel/stripe intersection area table) between the ray approximated by the stripe and the pixels, for example. However, other techniques and/or models for forward projecting image data to generate projection data are known to those skilled in the art and are contemplated for use herein.

It will be appreciated that while a single forward projection component 406 is illustrated herein, in other embodiment, more than one forward projection component may be used. For example, in another embodiment, the image reconstructor 400 comprises two forward projection components, with a first forward projection component configured to forward project the isolated regions 454 of the image data 452 and a second forward projection component configured to forward project the other regions 460 of the image data 452 and/or to forward project the image data 452 (e.g., including the isolated regions 454 such that the isolated regions 454 of the image data 452 are forward projected by both forward projection components).

The example image reconstructor 400 further comprises a projection correction component 408 configured to receive the measured projection data 450 and the inconsistent projection data 456 and to correct inconsistencies in the measured projection data caused by aspects of the object that commonly generate inconsistencies in measured projection data 450 using the inconsistent projection data 456. For example, in one embodiment, portions of the measured projection data 450 that are indicative of aspects of the object that generate inconsistencies in the measured projection data 450 are modified using the inconsistent projection data 456 indicative of those aspects. Stated differently, in one example, measured projection data 450 is corrected by modifying portions of the measured projection data 450 that are inconsistent with portions of the inconsistent projection data 456 indicative of a substantially similar (e.g., same) aspect of the object. The equation used to modify the inconsistent portions of the measured projection data can be derived using a physical model of X-ray propagation in different materials and/or using other modeling techniques, for example. In this way, the projection correction component 408 corrects the measured projection data 450, or rather corrects inconsistent aspects of the measured projection data 450, and generates corrected projection data 458 that comprises the corrected, measured projection data (e.g., with the inconsistent data being at least partially corrected to make it more consistent).

The image updater 402 is configured to receive the synthesized projection data 462 (e.g., indicative of regions 460 of the image data 452 that are not representative of aspects that generate inconsistencies in the measured projection data 450) and the corrected projection data 458. The image updater 402 is also configured to update the image data 452 based upon the synthesized projection data 462 and the corrected projection data 458 (e.g., which is similar to the measured projection data 450, but has been be corrected to account for portions of the measured projection data 450 that are inconsistent due to aspects of the object with a higher density and/or z-effective, for example), if corrected projection data 458 exists. Otherwise, the image updater 402 may update the image data 452 based upon a comparison of the synthesized projection data 462 and the measured projection data 450. Stated differently, as will be described below, in some embodiments, measured projection data 450 may not be corrected until several iterations have occurred, and thus during the iterations that occur before the measured projection data 450 is corrected, the image updater 402 may be configured to update the image data 452 merely based upon a comparison of the measured projection data 450 and the synthesized projection data 462, for example.

As described with respect to FIG. 3, the comparison of the synthesized projection data 456 and the corrected projection data 458 (or measured projection data 450) may be based on a cost function, representing a penalty on the data mismatch between the corrected projection data 458 (e.g., or measured projection data 450) and the synthesized projection data 456, and the reconstructed image (e.g., the image update that is applied) may be chosen to reduce and/or minimize the cost function. However, other formulations and/or image adjustment approaches, including image update strategies without explicit cost function definitions, are known to those skilled in the art and are also contemplated for use herein. Moreover, it will be appreciated that based upon which algorithm(s) is used to perform the update, pixels comprised in the image data 452 may be updated concurrently and/or in series. For example, in a pixel parallel simultaneous image update scheme, substantially all of the pixels are updated concurrently at respective iterations. However, other pixel update schemes are known to those skilled in the art and are contemplated for use herein.

The acts of identifying regions 454 in the image data 452 indicative of aspects of the object that generate inconsistencies in the measured projection data 450, forward projecting the identified regions 454 and other regions 460 of the image data 452, correcting the measured projection data 450 and/or, during subsequent iterations, correcting the corrected projection data 458, and comparing the corrected projection data 458 to the synthesized projection data 462 to update the image data used by the image updater 402 may be repeated until a specified outcome has been achieved, at which point the image updater 402 may transmit finalized image data 464 (e.g., 256 in FIG. 2) to a terminal (e.g., 126 in FIG. 1), for example. Stated differently, the image updater 402 may continue to output the image data 452 and receive synthesized projection data 462 indicative of more recently updated image data 452 to refine the image data (e.g., or the assumptions made in the conversion of the measured projection data 450 and/or corrected projection data 458 to image data 452) until a specified outcome has been achieved. As used herein, a specified outcome references stopping criteria which may comprise, but is not limited to, a specified number of iterations, an acceptable deviation threshold between the synthesized projection data 462 and the measured projection data 450 and/or the corrected projection data 458, etc.

It will be appreciated that while example image reconstructor 400 illustrates a component block diagram that describes the image updater 402 as transmitting the image data 452 to the inconsistency detector 404, in one embodiment, during one or more iterations the image updater 402 may bypass the inconsistency detector and transmit the image data 452 to the forward projection component 406. That is, inconsistent regions 454 of the image data 452 may be isolated in fewer than all of the iterations. Additionally, the measured projection data 450 or the corrected projection data 458 (e.g., if the measured projection data 450 has already been corrected in one or more iterations) may be corrected in fewer than all of the iterations. That is, the diagram, or loop, illustrated in FIG. 4 may be executed at selected iterations (e.g., which may include all of the iterations or fewer than all of the iterations). For remaining iterations, where the loop diagram illustrated in FIG. 4 is not executed, the diagram illustrated in FIG. 2 may be executed, for example.

Figure 5:
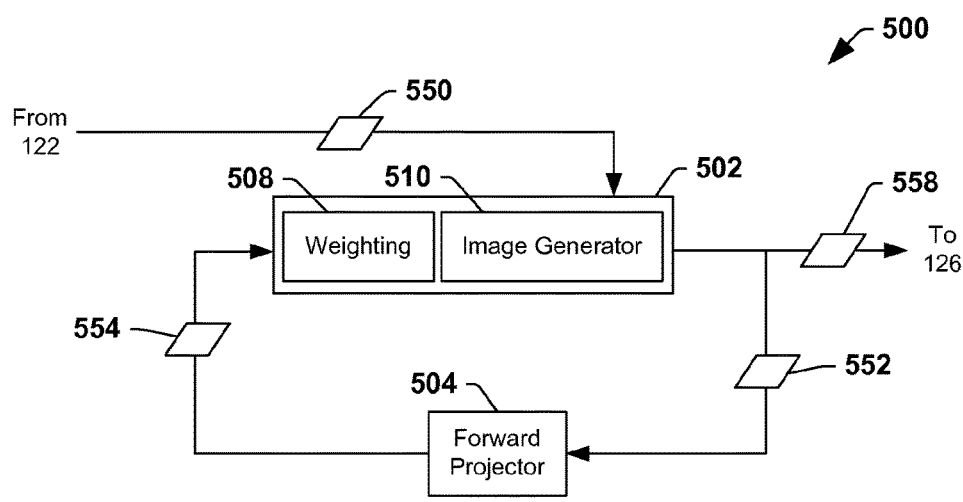
FIG. 5 illustrates a schematic block diagram illustrating an example environment of an image reconstructor.

FIG. 5 illustrates a schematic block diagram of another example image reconstructor 500 (e.g., 124 in FIG. 1) that is configured to reconstruct image data (e.g., images) through successive image refinements. Like the image reconstructor 200 illustrated in FIG. 2, the image reconstructor 500 comprises an image updater 502 (e.g., 402 in FIG. 4) configured to receive measured projection data 550 from a data acquisition component (e.g., 122 in FIG. 1), for example. As described above, the image updater 502 is configured to provide two substantially distinct functions. Initially, when the measured projection data 550 is first received, the image updater 502 is configured to convert the measured projection data 550 into initial image data 552 using analytic algorithms known to those skilled in the art. Subsequently (e.g., once image data 552 has been initially created), the image updater 502 is configured to update the image data 552 by comparing the measured projection data to the synthesized projection data (e.g., described hereforth) using the same and/or different algorithms relative to those used to initially generate image data 552. For simplicity in the figures, the initial image data and updated image data (e.g., that is generated at successive iterations after the initial image data is generated) are both referenced by character reference 552.

The image reconstructor 500 further comprises a forward projector 504 (e.g., 306 in FIG. 3) configured to receive the image data 552 and to convert or forward project the image data 552 using forward projection techniques known to those skilled in the art to generated synthesized projection data 554 (e.g., 254 in FIG. 2). For example, in one embodiment, the forward projection for a given ray is computed as a sum of the pixels intersected by the ray (e.g., which may be modeled by a stripe). The contribution of respective pixels may be computed as an intersection area (e.g., computed at run-time using a tabulated pixel/stripe intersection area table) between the ray approximated by the stripe and the pixels, for example. However, other techniques and/or models for forward projecting image data to generate projection data are known to those skilled in the art and are contemplated for use herein.

As illustrated, in the example image reconstructor 500, in one embodiment, the image updater 502 may be comprised of a plurality of components that assist in generating the image data 552 from the measured projection data 550 and/or in updating the image data 552 based upon the synthesized projection data 554, for example. More specifically, the example image updater 502 comprises a weighting component 508 and an image generator 510.

The weighting component 508 is configured to identify a degree of inconsistency in respective projections of the measured projection data 550 for respective channels of a detector array (e.g., 106 in FIG. 1). It will be appreciated that as described above with respect to FIG. 4, projections (e.g., and thus projection data yielded from the projections) may become inconsistent due to the interaction of radiation with aspects of an object having certain properties or characteristics. For example, highly dense aspects of an object and/or aspects of an object that comprise materials having a high atomic number may result in photon starvation and/or a phenomenon referred to in the art as beam hardening (e.g., where a disproportionate amount of lower energy photons are absorbed relative to an amount of higher energy photons that pass through the object), which may result in inconsistencies in one or more projections and thus in the measured projection data 550. Therefore, the weighting component 508 is configured to identify a degree of inconsistency in respective projections of the measured projection data 550 using techniques known to those skilled in the art.

Once the degree of inconsistency in respective projections is identified, the weighting component 508 may be further configured to determine a weight for respective channels of the detector in order to selectively weight measured projections yielded from one or more channels of the detector array more than measured projections yielded from other channels. In this way, some projections in the measured projection data 550 are selectively weighted more than other projections. That is, stated differently, a first part of a view of the object (e.g., comprised in the measured projection data 550) is weighted differently than other parts of the same view. In this way, when the image generator 510 aspect of the image updater 502 converts the measured projection data 550 into image data 552 and/or updates the image data 552, projections of the measured projection data 550 that are weighted more heavily (e.g., and are thus more consistent) influence the image update (e.g., and the resulting image data 552) more than projections that have a higher degree of inconsistency. Thus, by weighting the projections the image data 552 may be comprise fewer artifacts, for example, because projections that may cause artifacts in the image data 552 are discounted (e.g., or the influence of those projections on the image data 552 are reduced).

It will be appreciated that numerous techniques are contemplated for weighting the measured projection data 550. For example, in one embodiment, the measured projection data 550 is weighted before the measured projection data 550 is initially converted into image data 552 and the weighting is merely based upon the degree of inconsistency in respective projections that is identifiable in the measured projection data 550. In another embodiment, the degree of inconsistency in respective projections is identified based upon the synthesized projection data 554 and/or the image data 552 representative of the object under examination. For example, in one embodiment, an orientation of an aspect of the object which generates inconsistencies in the measured projection data 550 (e.g., and thus in one or more projections respectively yielded from one or more channels of the detector array) is identified in the image data 552.

By way of example, suppose the object comprises a solid, rectangular metal block having a depth of 1 cm, a length of 10 cm, and a width of 5 cm. It may be appreciated that the projections indicative of radiation that traversed the length of the block may have a higher degree of inconsistency than the projections indicative of radiation that traversed the width of the block, which may have a higher degree of inconsistency than the projections indicative of radiation that traversed the depth of the block because beam hardening occurs more commonly in denser materials (e.g., and 10 cm of metal is more dense than 5 cm of metal, which is more dense than 1 cm of metal). Therefore, in one embodiment, the weighting component 508 determines the orientation of the block from the image data 552 and weights projections yielded from channels that measured radiation passing through the depth of the block more than projections yielded from channels that measured radiation passing through the width of the block, and the projections yielded from channels that measured radiation passing through the width of the block can be weighted more than projections yielded from channels that measured radiation passing through the length of the block (e.g., which may be disregarded altogether), for example. In this way, projections that generally have a lower degree of inconsistency in the measured projection data 550 are given more weight than projections that have a higher degree of inconsistency (e.g., and thus less accurately represent the aspect of the object the projection is intended to represent).

The image generator 510 of the image updater 502 is configured to use the weighting(s) determined by the weighting component 508, the synthesis projection data 554 and/or the measured projection data 550 to update the image data 552. For example, in one embodiment, the image generator 510 may be configured to update equations/algorithms (e.g., described with respect to FIG. 3) used to update the image data 552 based upon the weights determined by the weighting component 508. Moreover, once the equations/algorithms are updated, the image generator 510 may be further configured to compare synthesized projection data 554 and the measured projection data 550 using the updated equations/algorithms to update the image data 552.

The acts of forward projecting the image data 552, determining the weights of the measured projection data 550, and updating the image data 552 based upon a comparison of the synthesized projection data 554 to the measured projection data 550 (e.g., using weights if the weights have been determined by the weighting component 508) may be repeated until a specified outcome has been achieved, at which point the image updater 502 may transmit finalized image data 558 (e.g., 256 in FIG. 2) to a terminal (e.g., 126 in FIG. 1), for example. Stated differently, the image updater 502 may continue to output the image data 552 and receive synthesized projection data 554 indicative of more recently updated image data 552 to refine the image data 552 until a specified outcome has been achieved. As used herein, a specified outcome references stopping criteria which may comprise, but is not limited to, a specified number of iterations, an acceptable deviation threshold between the synthesized projection data 554 and the measured projection data 550 and/or the weighted projection data, etc.

It will be appreciated that the set of weights for the measured projection data 550 does not have to be determined during each of the iterations That is, the diagram, or loop, illustrated in FIG. 5 may be executed at selected iterations (e.g., which may include all of the iterations or fewer than all of the iterations). For remaining iterations, the measured projection data 550 may not be weighted and/or the weights that have been previously established may be reused, for example.

It will also be appreciated that while the example image reconstructors 300, 400, and 500 illustrated in FIGS. 3, 4, and 5 respectively comprise components not illustrated in the other image reconstructors, components from two or more of the illustrated image reconstructors may be combined to form an image reconstructor. For example, in another embodiment, the image reconstructor (e.g., 124 in FIG. 1) comprises the regularization component 304 illustrated in FIG. 3 and the inconsistency detector 404 and projection correction component 408 illustrated in FIG. 4. In another embodiment, the image reconstructor may comprise the regularization component 304 illustrated in FIG. 3 and the weighting component 508 illustrated in FIG. 5, for example. In yet another embodiment, the image reconstructor may comprise the inconsistency detector 404 and projection correction component 408 illustrated in FIG. 4 and the weighting component 508 illustrated in FIG. 5. Thus, FIGS. 3-5 merely illustrate example configurations of an image reconstructor and other image reconstructors which can be formed based upon the combination of components illustrated in FIGS. 3-5 are also contemplated herein.

Figure 6:
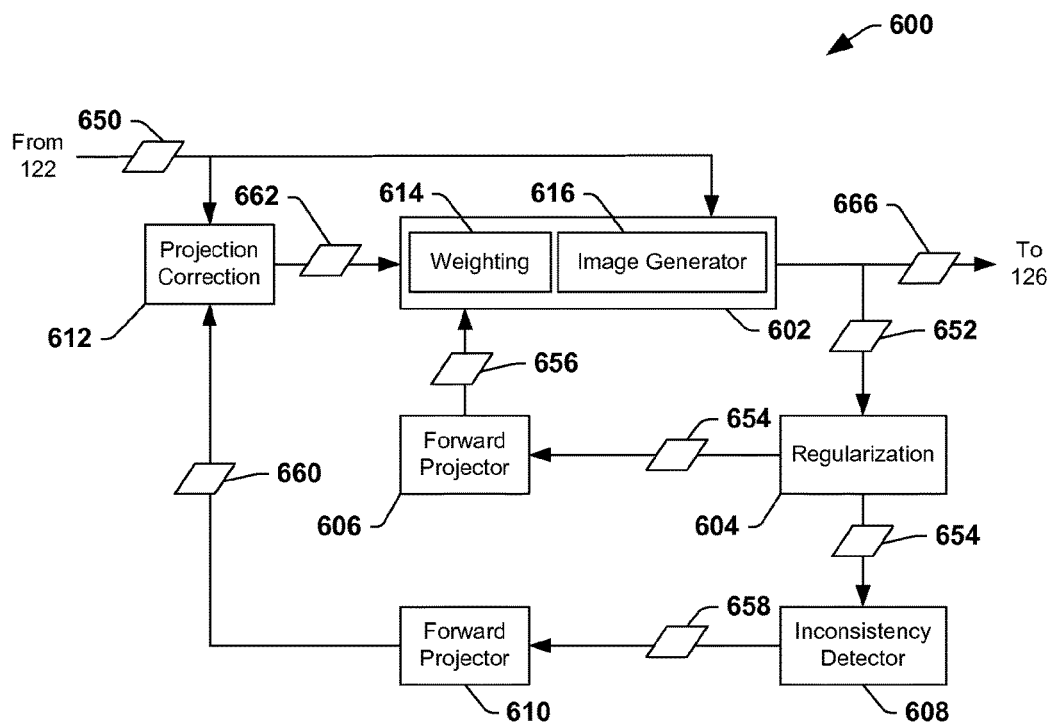
FIG. 6 illustrates a schematic block diagram illustrating an example environment of an image reconstructor.

FIG. 6 illustrates a schematic block diagram of yet another example image reconstructor 600 (e.g., 124 in FIG. 1) (e.g., such as may be formed by combining components of the image reconstructors illustrated in FIGS. 3-5). More specifically, FIG. 6 illustrates a block diagram illustrating an image reconstructor 600 that may be formed by combining the image reconstructor elements illustrated in FIGS. 3-5. It will be appreciated that the example diagram merely illustrates one example schematic and it is not intended limit the scope of the disclosure, including the claims, to the extent practicable.

As illustrated, the image reconstructor 600 comprises an image updater 602 configured to receive measured projection data 650 from a data acquisition component (e.g., 122 in FIG. 1). The image updater 602 is also configured to initially reconstruct image data 652 from the measured projection data and subsequently update the image data 652 during respective iterations using one or more algorithms known to those skilled in the art as described above.

The image reconstructor 600 also comprises a regularization component 604 configured to receive and regularize the image data 652 to generate regularized image data 654. As described with respective to FIG. 3, the term "regularize" and/or the like is used herein in a broad sense to refer to modifying and/or smoothing, etc. the image data 652 and/or one or more specified quality metrics, such as resolution, modulation transfer function, noise, artifacts, and/or streaks, etc. for example, in the image data 652. For example, regularizing the image data 652 may comprise filtering the image data 652 using a low pass filter to smooth the image data 652. However, other filtering techniques and/or, more generally, regularization techniques known to those skilled in the art for modifying the image data 652 and/or one or more quality metrics of the image data 652 are also contemplated herein.

The image reconstructor 600 further comprises a first forward projector 606 (e.g., 204 in FIG. 2) configured to receive the regularized image data 654 and convert, or forward project, the regularized image data 654 to generate synthesized projection data 656 (e.g., 254 in FIG. 2) using forward projection techniques known to those skilled in the art (e.g., as described in FIGS. 2-5).

The image reconstructor 600 further comprises an inconsistency detector 608 configured to identify regions of the regularized image data 654 that represent aspects of an object that generate inconsistencies (e.g., artifacts) in the measured projection data 650 and to isolate the identified regions 658 of the regularized image data 654. For example, as described with respect to FIG. 4, the inconsistency detector 608 may be configured to determine a value for respective voxels and/or pixels corresponding to a property of the object that causes inconsistencies. For example, the inconsistency detector 608 may determine a CT number (e.g., density value) or z-effective value for respective voxels and/or pixels of the regularized image data 654. The inconsistency detector 608 may then threshold the regularized image data 654 and segment voxels and/or pixels comprised in the regularized image data 654 with values greater than a specified threshold from the regularized image data 654. In will be appreciated that the voxels and/or pixels with values less than the specified threshold may be masked and/or discarded (e.g., such that merely isolated regions 658 of the regularized image data 654 are visible in the image data output by the inconsistency detector 608).

The image reconstructor 600 also comprises a second forward projection component 610 configured to receive the isolated regions 658 of the regularized image data 654 and convert, or forward project, the isolated regions 658 to generate inconsistent projection data 660 (e.g., 456 in FIG. 4) using forward projection techniques known to those skilled in the art (e.g., as described in FIGS. 2-5).

It will be appreciated from the illustration that while the first forward projection component 606 is configured to forward project substantially all of the regularized image data 654, the second forward projection component 610 merely forward projects the isolated regions 658 of the regularized image data 654 that have been identified by the inconsistency detector 608 as regions that represent aspects of the object that generate or may generate inconsistencies in the measured projection data 650. Thus, the synthesized projection data 656 yielded from the first forward projection component 606 is indicative of (e.g., represents) the (e.g., regularized) object under examination whereas the inconsistent projection data 660 yielded from the second forward projection component 610 is merely indicative of aspects (e.g., portions) of the object that generate inconsistencies in the measured projection data such as high density aspects and/or aspects that are comprised of materials with high atomic numbers, for example.

The inconsistent projection data 660 is transmitted to a projection correction component 612 (e.g., 408 in FIG. 4) configured to correct inconsistencies in the measured projection data 650 (e.g., caused by aspects of the object that commonly generate inconsistencies in measured projection data 650) using the inconsistent projection data 660. That is, the inconsistencies in the measured projection data 650 are corrected based upon the inconsistent projection data 660 using analytic algorithms and/or other correction techniques known to those skilled in the art (e.g., as described with respect to FIG. 4). In this way, corrected projection data 662 comprising corrections to the measured projection data 650 is generated, where the corrected projection data 662 comprises fewer inconsistencies than the measured projection data 650.

As illustrated in the example image reconstructor 600, in one embodiment, the image updater 602 may comprise a plurality of components that assist in generating the image data 652 from the measured projection data 650 and/or in updating the image data 652 based upon the synthesized projection data 656 and/or the corrected projection data 662, for example. More specifically, the image updater 602 of the example image reconstructor 600 comprises a weighting component 614 (e.g., 508 in FIG. 5) and an image generator 616 (e.g., 510 in FIG. 5).

The weighting component 614, as described above with respect to FIG. 5, is configured to identify a degree of inconsistency in respective projections (e.g., yielded from respective channels of the detector array), and to determine a set of weights for detectors based upon the identified degree of inconsistency such that projections with less of a degree of inconsistency (e.g., more consistent projections) are given more weight in the measured projection data 650 and/or the corrected projection data 662 than projections with a higher degree of inconsistency. In this way, when the image update component 602 converts the measured projection data and/or the corrected projection data 662, using determined weights, into image data 652, projections of the measured projection data 650 and/or the corrected projection data 662 that are weighted more heavily (e.g., and are thus more consistent) influence the image update (e.g., and the resulting image data 652) more than projections that have a higher degree of inconsistency. Thus, by using the set of weights, the image data 652 comprises fewer artifacts, for example, because projections that may cause artifacts in the image data 652 are discounted (e.g., or the influence of those projections on the image data 652 are reduced).

The image generator 616 is configured to use one or more algorithms (e.g., as described above) to generate and subsequently update the image data 652. It will be appreciated that where weights for respective detectors have been determined, in one embodiment (e.g., as described with respect to FIG. 5), the image generator 616 may be further configured to update the equations/algorithms used during the generation and/or updating of the image data 652 based upon the determined weights. In this way, projections yielded from detectors of the detector array that measured less inconsistency may be weighted more heavily during the generation/updating than other projections of the measured projection data that are indicative of a higher degree of inconsistency, for example.

The acts described herein may be repeated until a specified outcome has been achieved, at which point the image updater 602 may transmit finalized image data 666 (e.g., 256 in FIG. 2) to a terminal (e.g., 126 in FIG. 1), for example. Stated differently, the data may continue to flow through the loop illustrated in FIG. 6 until a specified outcome has been achieved. As used herein, a specified outcome references stopping criteria which may comprise, but is not limited to, a specified number of iterations, an acceptable deviation threshold between the synthesized projection data 656 and the measured projection data 650, etc.

It will be appreciated that as described in FIGS. 3-5, one or more of the components may be bypassed on one or more of the iterations. For example, the regions 658 of the regularized image data 654 representing aspects of the object that generate inconsistencies in the measured projection data may be isolated in merely a few of many iterations, for example, and/or the measured projection data 650 may be weighted by the weighting component 614 in merely the first iteration (e.g., before image data 652 is generated), for example.

Figure 7:
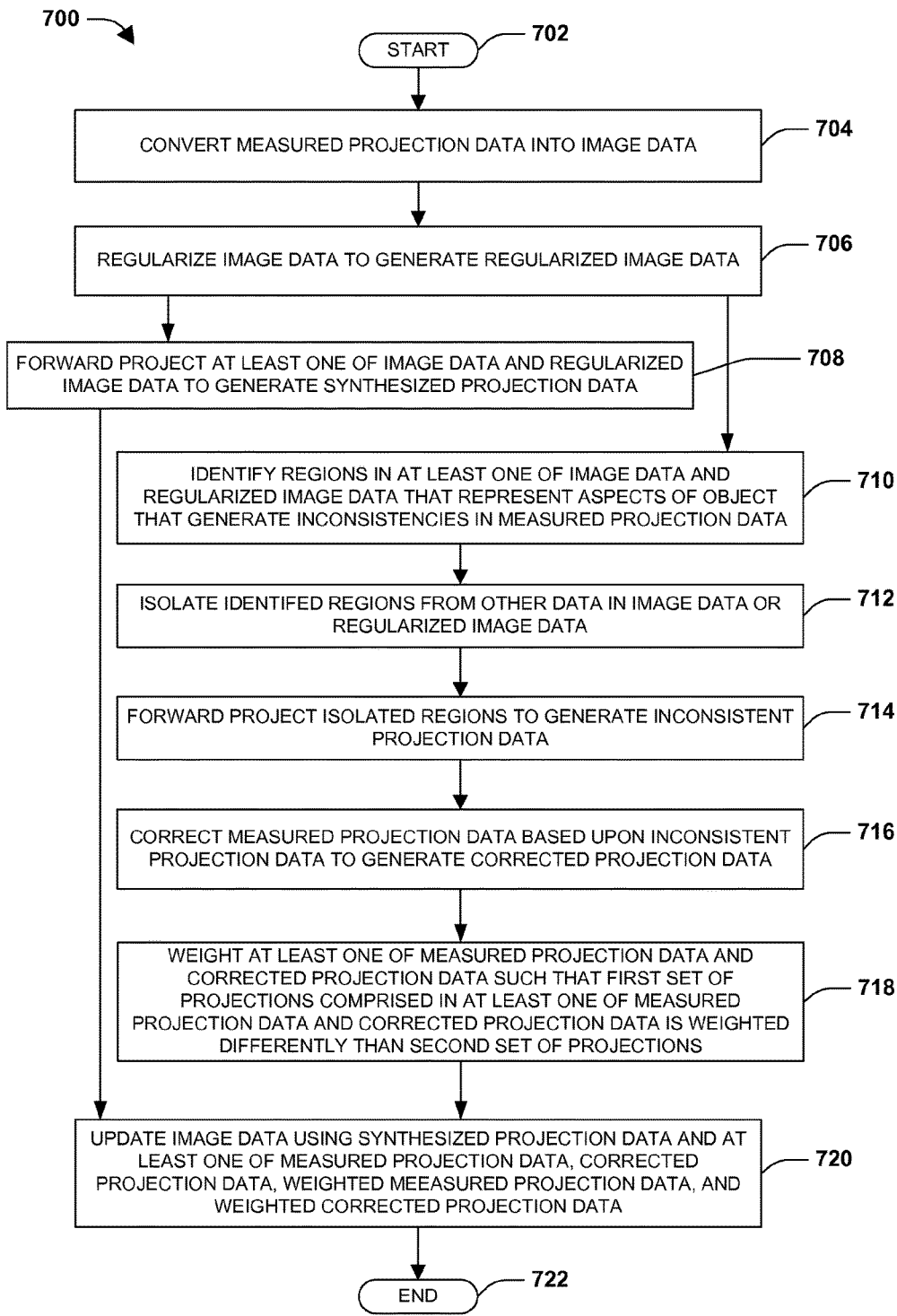
FIG. 7 is a flow diagram illustrating an example method for reconstructing one or more x-ray images of an object under examination from measured projection data indicative of the object.

FIG. 7 illustrates an example image reconstruction method 700 such as may be used to reconstruct images from projection data yielded from a CT examination of an object, for example. It will be appreciated that FIG. 7 is intended to illustrates one example method for image reconstruction and other methods, such as those described in the preceding diagrams, are contemplated herein. That is, some of the acts described in FIG. 7 are optional and/or may be applied optionally at select iterations while not being applied at other iterations. Moreover, it will be appreciated that some of the acts described below may be applied during a first set of iterations and other acts described below may be applied at other iterations.

The example method 700 begins at 702 and measured projection data is converted into initial image data at 704 using one or more of the analytical techniques known to those skilled in the art (e.g. 2D filtered back projection, 3D filtered back projection, etc.).

At 706 in the example method, the image data is regularized to generate regularized image data. It was appreciated that the term "regularize" and/or the like is used herein in a broad sense to refer to modifying and/or smoothing, etc. the image data and/or one or more specified quality metrics, such as resolution, modulation transfer function, noise, artifacts, and/or streaks, etc., for example, in the image data. For example, regularizing the image data may comprise filtering the image data using a low pass filter to smooth the image data. In one embodiment, such low pass filtering may comprise using a linear combination of the image data and a negative Laplacian operator applied to image data, for example. However, other filtering techniques or, more generally, regularization techniques known to those skilled in the art for modifying the image data and/or one or more quality metrics of the image data are also contemplated herein.

It will be appreciated that by modifying or regularizing the image data, the regularized image data differs from the image that would have been created by the measured projection data had the measured projection data been ideally converted into image data. Thus, the regularized image data, and finalized image data that results from the regularization(s) and image update(s) are intended to differ from an idealized image that would be generated from the measured projection data.

At 708 in the example method, at least one of the image data and the regularized image data is forward projected to generate synthesized projection data using forward projection techniques known to those skilled in the art. For example, in one embodiment, the forward projection for a given ray is computed as a sum of the pixels intersected by the ray (e.g., which may be modeled by a stripe). The contribution of respective pixels is computed as an intersection area (e.g., computed at run-time using a tabulated pixel/stripe intersection area table) between the ray approximated by the stripe and the pixels, for example. However, other techniques for forward projecting image data to generate synthesized projection data are known to those skilled in the art and are contemplated for use herein.

It will be appreciated that as described above, the synthesized projection data is intended to accurately (e.g., exactly) represent the regularized image data.

It will also be appreciated whether the image data or the regularized image data is forward projected at 708 may depend upon whether the act described in 706 is performed. That is, in another embodiment of the example method 700, the image data is not regularized in one or more iterations of the example method 700, and the image data (e.g., as opposed to the regularized image data) is forward projected to generate synthesized projection data 708. Thus, either the regularized image data or the image data may be forward projected at 708 depending upon whether the image data was regularized at 706, for example.

At 710 in the example method 700, regions in at least one of the image data and the regularized image data that represent or may represent aspects of the object that generate inconsistencies (e.g., artifacts) in the measured projection data are identified. It will be appreciated that regions of the image data that represent aspects of the object that generate inconsistencies in the measured projection data are generally the same regions as those in the regularized image data that represent aspects of the object that generate inconsistencies in the measured projection data. However, as described above, in one or more iterations of the example method 700, the image data may not be regularized and thus the regions in the image data (e.g., as opposed to regions in the regularized image data) may be identified.

It will be appreciated to those skilled in the art that inconsistencies in the measured projection data are generally caused by aspects of the object that have particular characteristics or properties. For example, aspects of the object that comprise materials having a higher density (e.g., such as steel) and/or a higher z-effective (e.g., such as mercury) may create inconsistencies in the measured projection data as a result of photon starvation and/or beam hardening, for example. That is, inconsistencies are created in the measured projection data 450 because of phenomenon that occur when aspects of the object are comprised of certain materials (e.g., high density, high atomic number materials, etc.). For example, high density materials (e.g., such as some metals) absorb a disproportionate amount of lower energy photons causing the high density material to appear in the measured projection data as a lower density material and resulting in an inconsistency in the measured projection data.

The example method 700 is configured to identify such regions at 710 using analytic, iterative, or other techniques known to those skilled in the art. In one embodiment, identifying the regions comprises determining a value for respective voxels or pixels in the image data and/or the regularized image data corresponding to a property of the object that causes inconsistencies. For example, a CT number (e.g., density value) or z-effective value may be determined for respective voxels and/or pixels of the image data and/or the regularized image data. Voxels and/or pixels that are determined to have a CT number and/or a z-effective value greater than a specified threshold may be identified at 710 as corresponding to a region(s) that represents an aspect of the object that generates inconsistencies (e.g., or is more likely to generate inconsistencies) in the measured projection data.

At 712 in the example method 700, the identified regions that represent or may represent aspects of the object that generate inconsistencies in the measured projection data are isolated from other portions of the data in the image data and/or the regularized image data (e.g., depending upon whether the regions were identified in the image data or the regularized data). For example, in one embodiment the voxels and/or pixels that were identified as having a CT number and/or a z-effective value greater than a specified threshold may be segmented from the voxels and/or pixels with a CT number and/or z-effective value less than or equal to the specified threshold. Moreover, the voxels and/or pixels with a CT number and/or z-effective value less than or equal to the specified threshold may be masked (e.g., or otherwise discarded) in the image data and/or the regularized image data, for example.

At 714 in the example method 700, the isolated regions of the image data and/or the regularized image data are forward projected to generate inconsistent projection data using forward projection techniques known to those skilled in the art (e.g., which may be the same forward projection techniques as used to forward project the regularized image data at 708). For example, in one embodiment, the forward projection for a given ray is computed as a sum of the pixels intersected by the ray (e.g., which may be modeled by a stripe). The contribution of respective pixels is computed as an intersection area (e.g., computed at run-time using a tabulated pixel/stripe intersection area table) between the ray approximated by the stripe and the pixels, for example. However, other techniques for forward projecting isolated regions of the image data and/or the regularized image data to generate inconsistent projection data are known to those skilled in the art and are contemplated for use herein.

It will be appreciated that the phrase "inconsistent projection data" and/or the like is used herein to describe projection data that is indicative of the regions of the image data that represent aspects of the object that caused or may have caused inconsistencies in the projection data. Other portions of the image data and/or the regularized image data are not forward projected at 714 because they were masked or otherwise discarded at 712. However, it is to be understood that the regularized image data (e.g., in its entirety including the isolated regions and the masked portions) and/or the image data (e.g., if the image data was not regularized) was forward projected at 708. Thus, the isolated regions may be forward projected twice, once at 708 and again at 714.

At 716 in the example method 700, the measured projection data is corrected based upon the inconsistent projection data to generate corrected projection data. For example, in one embodiment, portions of the measured projection data that are indicative of aspects of the object that generate inconsistencies in the measured projection data are modified by the inconsistent projection data indicative of those aspects. Stated differently, in one example, measured projection data is corrected by modifying portions of the measured projection data that are inconsistent using portions of the inconsistent projection data indicative of a substantially similar (e.g., same) aspect of the object. In this way, the measured projection data, or rather inconsistent aspects of the measured projection data, is corrected to reduce the number and/or degree of inconsistencies in the measured projection data, for example.

It will be appreciated that in another embodiment, regions of the image data and/or regions of the regularized image data are not identified at 710 in one or more iterations of the example method 700, and the acts described at 710, 712, 714, and 716 may not be comprised in one or more iterations of the example method 700 (e.g., including not being performed in any the iterations). Thus, the acts described at 710, 712,714, and 716 may be optionally performed at selective iterations, for example.

At 718, at least one of the measured projection data and the corrected projection data (e.g., if such data exists) is weighted such that a first set of projections comprised in the measured projection data and/or in the corrected projection data is assigned a weight which is different than a weight assigned to a second set of projections comprised in the measured projection data and/or in the corrected projection data. In this way set of weights for individual detectors may be generated, for example. In one example, a degree of inconsistency in respective projections of the measured projection data and in respective projections of the corrected projection data is identified and respective projections are weighted based upon their respective degree of inconsistency. For example, highly dense aspects of an object and/or aspects of an object that comprise materials having a high atomic number may result in photon starvation and/or a phenomenon referred to in the art as beam hardening (e.g., where a disproportionate amount of lower energy photons are absorbed relative to an amount of higher energy photons that pass through the object), which may result in inconsistencies in one or more projections and thus in the measured projection data and/or the corrected projection data. By identifying and weighting the projections according to their respective degree of inconsistency (e.g., such that projections that are more consistent are given greater weight), the image data may comprise fewer artifacts, for example, because projections that may cause artifacts in the image data are discounted (e.g., or the influence of those projections on the image data are reduced).

As noted with several of the other acts in the example method 700, the act of weighting projections at 718 is optional and may be selectively applied at all or fewer than all of the iterations (e.g., including at no iterations of the example method 700). For example, in one embodiment, the measured projection data is merely weighted at 718 before the measured projection data is initially converted into image data at 704, and during subsequent iterations of the example method 700, no weighting is applied to the measured projection data and/or the corrected projection data, for example.

At 720 in the example method, the image data is updated to generated updated image data using the synthesized projection data and at least one of the measured projection data, the corrected projection data, the set of weights (e.g., depending upon which acts of the example method 700 have been performed). For example, if merely the acts described in 704-708 have been performed, the image data may be updated based upon the synthesized projection data and the measured projection data. If the acts described in 704, 708, and 710-716 (e.g., and optionally the act described at 706) have been performed, the image data may be updated based upon the synthesized projection data and the corrected projection data. If the acts described in 704, 708, and 718 (e.g., and optionally the act described at 706) have been performed, the image may be updated based upon the synthesized projection data and the set of weights. If the acts described in 704, 708, and 710-718 (e.g., and optionally the act described in 706) have been performed, the image may be updated based upon the synthesized projection data and the set of weights, for example. Thus, the data used to perform the update may depend upon which actions have been performed in that particular iteration of the example method 700 and/or which actions have been performed in previous iterations, for example.

During the image update, similarities and/or the differences between the synthesized projection data and the other data (e.g., the measured projection data, the corrected projection data are identified and used to update image data.

It will be appreciated that the acts described above may be iteratively repeated (e.g., with all or fewer than all of the acts of the example method 700 being performed at respective iterations) until a specified outcome has occurred, at which time finalized image data may be output to a terminal and viewed by user, for example.

The example method 700 ends at 722.

Figure 8:
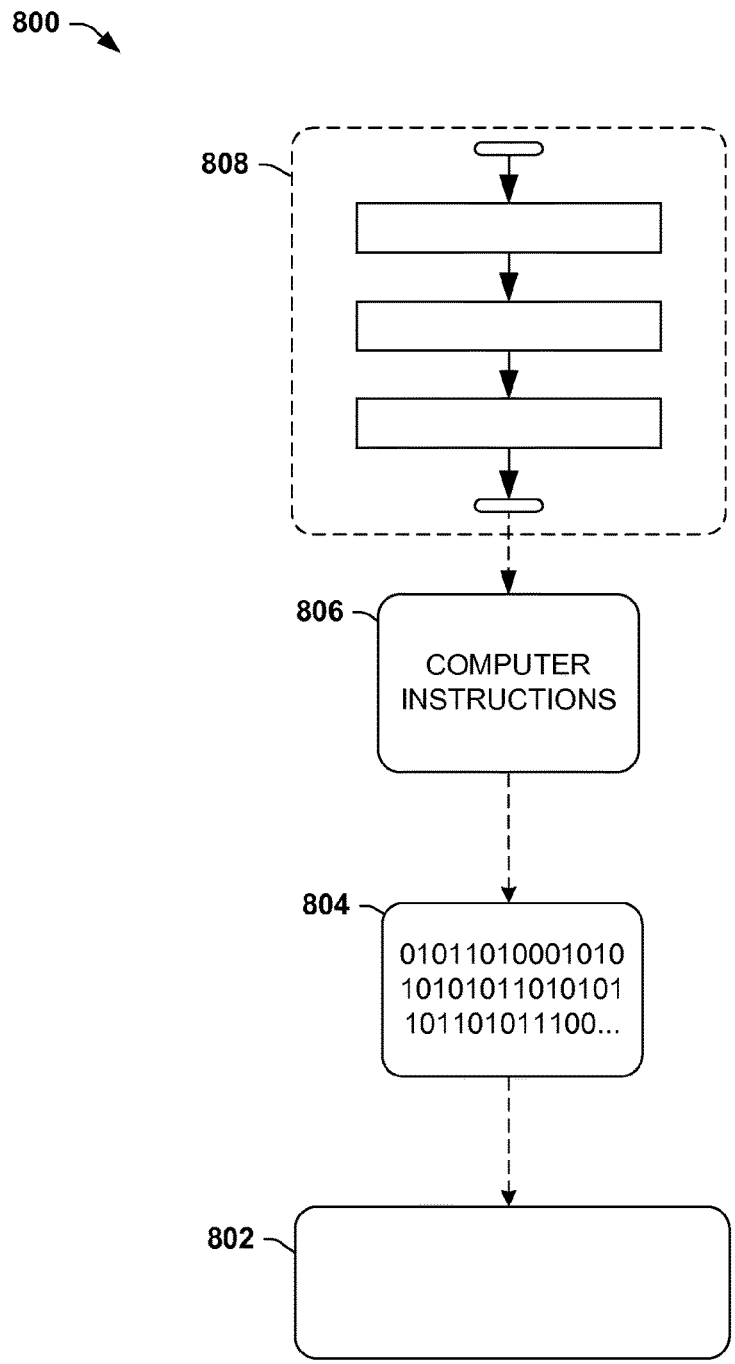
FIG. 8 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 8, wherein the implementation 800 comprises a computer-readable medium 802 (e.g., a CD-R, DVD-R, or a platter of a hard disk drive), on which is encoded computer-readable data 804. This computer-readable data 804 in turn comprises a set of computer instructions 806 configured to operate according to one or more of the principles set forth herein. In one such embodiment 800, the processor-executable instructions 806 may be configured to perform a method 808, such as at least some of the example method 700 of FIG. 7, for example. In another such embodiment, the processor-executable instructions 806 may be configured to implement a system, such as at least some of the exemplary environment 100 of FIG. 1, for example. Many such computer-readable media may be devised by those of ordinary skill in the art that are configured to operate in accordance with one or more of the techniques presented herein.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method for reconstructing an x-ray image of an object under examination from measured projection data indicative of the object, comprising:
converting the measured projection data into image data to generate a first instance of the image data;
regularizing the first instance of the image data to generate regularized image data, wherein the regularizing comprises selecting a first quality metric in the image data for modification based upon a type of object of focus during the examination and selecting a second quality metric in the image data for modification based upon the type of object of focus during the examination, the second quality metric different than the first quality metric;
isolating a region of the regularized image data that represents an aspect of the object that generates an inconsistency in the measured projection data;
forward projecting the region to generate inconsistent projection data;
forward projecting a portion of the regularized image data not corresponding to the region to generate a first instance of synthesized projection data, wherein the first instance of the first instance of the synthesized projection data excludes a forward projection of the region;
correcting the measured projection data based at least in part upon the inconsistent projection data to generate corrected projection data; and
updating the image data to generate a second instance of the image data using the corrected projection data and using the first instance of the synthesized projection data.

2. The method of claim 1, comprising forward projecting the second instance of the image data to generate a second instance of the synthesized projection data.

3. The method of claim 1, the first quality metric and the second quality metric consisting of quality metrics selected from a group consisting of resolution, modulation transfer function, noise, artifacts, or streaks.

4. The method of claim 1, comprising identifying the region based at least in part upon at least one of a density characteristic or a z-effective characteristic of the aspect.

5. The method of claim 1, comprising selectively weighting portions of the measured projection data.

6. The method of claim 5, the selectively weighting comprising:
identifying a degree of inconsistency in measured projections, comprised in the measured projection data, for one or more channels of a detector array; and
weighting a first measured projection of the measured projections yielded from a first channel of the one or more channels more than a second measured projection of the measured projections yielded from a second channel of the one or more channels based at least in part upon the degree of inconsistency in the measured projections, wherein the first measured projection and the second measured projection are parts of a same view.

7. A method for reconstructing an x-ray image of an object under examination from measured projection data indicative of the object, comprising:
isolating a region of image data, yielded from the measured projection data, which represents an aspect of the object that generates an inconsistency in the measured projection data;
forward projecting the region to generate inconsistent projection data;
forward projecting a portion of the image data not corresponding to the region to generate synthetized projection data, wherein the synthetized projection data excludes a forward projection of the region;
correcting the measured projection data based at least in part upon the inconsistent projection data to generate corrected projection data; and
updating the image data to generate updated image data using the corrected projection data and using the synthesized projection data.

8. The method of claim 7, the isolating comprising:
masking a second region of the image data that represents a second aspect of the object having a density that is less than or equal to a specified threshold.

9. The method of claim 7, the isolating comprising:
masking a second region of the image data that represents a second aspect of the object having a z-effective value that is less than or equal to a specified threshold.

10. The method of claim 7, the isolating comprising:
thresholding the image data; and
segmenting at least one of voxels or pixels comprised in the image data with values greater than a specified threshold such that at least one of a first voxel or a first pixel with a value less than or equal to the specified threshold is masked.

11. The method of claim 7, wherein the updating comprises comparing the synthesized projection data to the corrected projection data.

12. The method of claim 7, comprising selectively weighting portions of at least one of the measured projection data or the corrected projection data, comprising:
identifying a degree of inconsistency in measured projections, comprised in at least one of the measured projection data or the corrected projection data, for one or more channels of a detector array; and
weighting at least one of:
a first measured projection of the measured projections, comprised in the measured projection data and yielded from a first channel of the one or more channels, more than a second measured projection of the measured projections, comprised in the measured projection data and yielded from a second channel of the one or more channels, based at least in part upon the degree of inconsistency in the measured projections comprised in the measured projection data, or
a third measured projection of the measured projections, comprised in the corrected projection data and yielded from a third channel of the one or more channels, more than a fourth measured projection of the measured projections, comprised in the corrected projection data and yielded from a fourth channel of the one or more channels, based at least in part upon the degree of inconsistency in the measured projections comprised in the corrected projection data.

13. A system for reconstructing an x-ray image of an object under examination from measured projection data indicative of the object, comprising:
an image updater configured to convert the measured projection data into image data representative of the object;

an inconsistency detector configured to isolate a region of the image data that represents an aspect of the object that generates an inconsistency in the measured projection data;

a forward projection component configured to forward project the region to generate inconsistent projection data and to forward project a portion of the image data not corresponding to the region to generate synthesized projection data; and a projection correction component configured to correct the measured projection data based at least in part upon the inconsistent projection data to generate corrected projection data, the image updater configured to update the image data based at least in part upon the corrected projection data and the synthesized projection data.

14. The system of claim 13, comprising a regularization component configured to regularize the image data to generate regularized image data, regularizing the image data comprising modifying one or more specified quality metrics in the image data.

15. The system of claim 14, the forward projection component configured to project the regularized image data into the synthesized projection data.

16. The system of claim 14, the regularization component configured to select the one or more specified quality metrics in the image data based upon a type of object of focus during the examination.

17. The method of claim 1, wherein the updating comprises comparing the corrected projection data to the first instance of the synthesized projection data.

18. The method of claim 1, the updating comprising selectively weighting portions of the corrected projection data.

19. The method of claim 18, comprising:

identifying a degree of inconsistency in measured projections, comprised in the corrected projection data, for one or more channels of a detector array; and weighting a first measured projection of the measured projections, comprised in the corrected projection data and yielded from a first channel of the one or more channels, more than a second measured projection of the measured projections, comprised in the corrected projection data and yielded from a second channel of the one or more channels, based at least in part upon the degree of inconsistency in the measured projections comprised in the corrected projection data.

20. The method of claim 1, the isolating comprising:

thresholding the regularized image data; and segmenting at least one of voxels or pixels comprised in the regularized image data with values greater than a specified threshold such that at least one of a first voxel or a first-pixel with a value less than or equal to the specified threshold is masked.

\* \* \* \* \*